US00PP34159P2

(12) United States Plant Patent
Winslow

(10) Patent No.: US PP34,159 P2
(45) Date of Patent: Apr. 19, 2022

(54) ***LOBELIA* PLANT NAMED 'WNLOLACLWH'**

(50) Latin Name: *Lobelia erinus*
Varietal Denomination: WNLOLACLWH

(71) Applicant: Benjamin Kent Winslow, Buda, TX (US)

(72) Inventor: Benjamin Kent Winslow, Buda, TX (US)

(73) Assignee: WINGEN, LLC, Mustang Ridge, TX (US)

( * ) Notice: Subject to any disclaimer, the term of this patent is extended or adjusted under 35 U.S.C. 154(b) by 0 days.

(21) Appl. No.: 17/371,918

(22) Filed: Jul. 9, 2021

(51) Int. Cl.
*A01H 5/02* (2018.01)
*A01H 6/26* (2018.01)

(52) U.S. Cl.
USPC ..... Plt./451

(58) Field of Classification Search
USPC ..... Plt./263.1, 451
See application file for complete search history.

*Primary Examiner* — Susan McCormick Ewoldt
*Assistant Examiner* — Karen M Redden
(74) *Attorney, Agent, or Firm* — C. Anne Whealy

(57) ABSTRACT

A new and distinct cultivar of *Lobelia* plant named 'WNLOLACLWH', characterized by its upright to outwardly spreading and mounding to trailing plant habit; vigorous and sturdy growth habit; freely branching habit; dense and bushy plant form; freely flowering habit; long flowering period; pure white-colored flowers; long flowering period; relative high temperature tolerance and good garden performance.

2 Drawing Sheets

Figure 1:
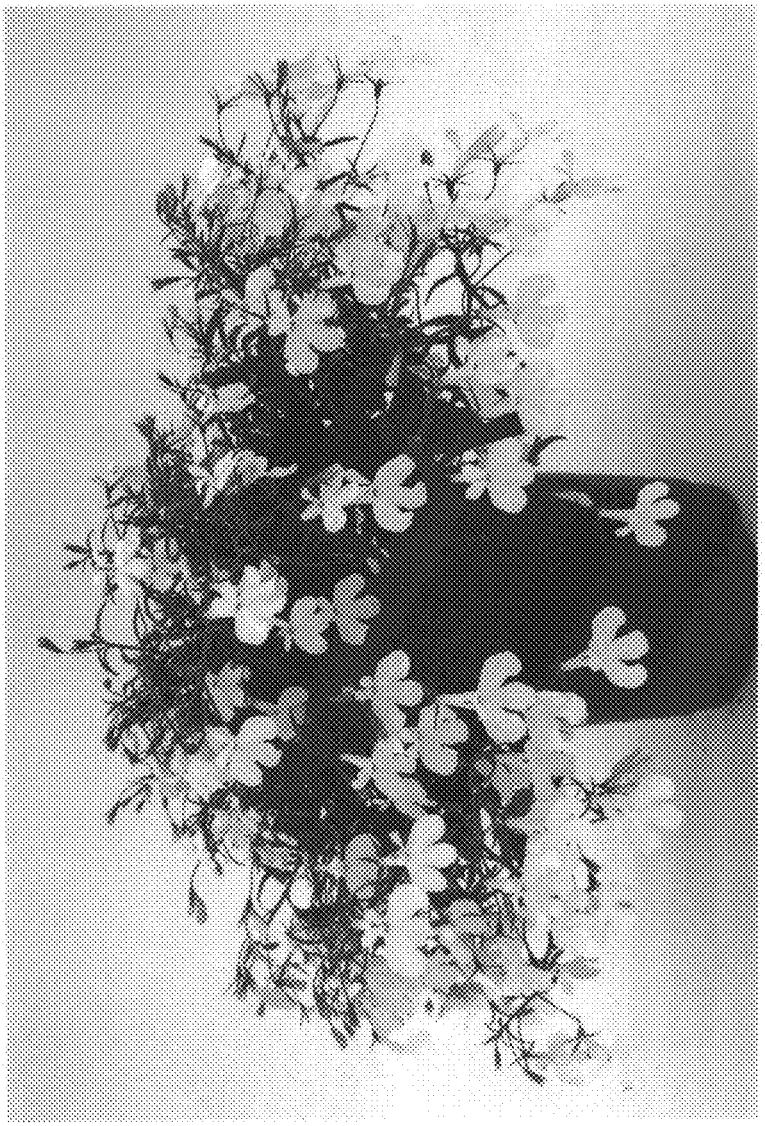

Botanical designation: *Lobelia erinus.*
Cultivar denomination: 'WNLOLACLWH'.

BACKGROUND OF THE INVENTION

The present invention relates to a new and distinct cultivar of *Lobelia* plant, botanically known as *Lobelia erinus* and hereinafter referred to by the name 'WNLOLACLWH'.

The new *Lobelia* plant is a product of a planned breeding program conducted by the Inventor in Alajuela, Costa Rica, Twinsburg, Ohio and Carleton, Mich. The objective of the breeding program is to create new outwardly spreading, freely-branching and bushy *Lobelia* plants with a long flowering period, high temperature tolerance and good garden performance.

The new *Lobelia* plant originated from a cross-pollination made by the Inventor in Alajuela, Costa Rica in November, 2016 of *Lobelia erinus* 'Tech Hewhit', disclosed in U.S. Plant Pat. No. 19,053, as the female, or seed, parent with *Lobelia erinus* 'Weslosnowhi', not patented, as the male, or pollen, parent. The new *Lobelia* plant was discovered and selected by the Inventor as a single flowering plant within the progeny of the stated cross-pollination in a controlled greenhouse environment in Twinsburg, Ohio on Aug. 15, 2017.

Asexual reproduction of the *Lobelia* plant by vegetative terminal cuttings in Carleton, Mich. since Nov. 15, 2017 has shown that the unique features of this new *Lobelia* plant are stable and reproduced true to type in successive generations.

SUMMARY OF THE INVENTION

Plants of the new *Lobelia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'WNLOLACLWH'. These characteristics in combination distinguish 'WNLOLACLWH' as a new and distinct *Lobelia* plant:

1. Upright to outwardly spreading and mounding to trailing plant habit.
2. Vigorous and sturdy growth habit.
3. Freely branching habit; dense and bushy plant form.
4. Freely flowering habit.
5. Long flowering period.
6. Pure white-colored flowers.
7. Long flowering period.
8. Relative high temperature tolerance and good garden performance.

Plants of the new *Lobelia* differ primarily from plants of the female parent, 'Tech Hewhit', in the following characteristics:

1. Plants of the new *Lobelia* are more high temperature tolerant than plants of 'Tech Hewhit'.
2. Plants of the new *Lobelia* have larger flowers than plants of 'Tech Hewhit'.

Plants of the new *Lobelia* differ primarily from plants of the male parent, 'Weslosnowhi', in the following characteristics:

1. Plants of the new *Lobelia* are more vigorous than and not as compact as plants of 'Weslosnowhi'.
2. Plants of the new *Lobelia* have larger flowers than plants of 'Weslosnowhi'.

Plants of the new *Lobelia* can be compared to plants of *Lobelia erinus* 'Loboudtis', disclosed in U.S. Plant Pat. No. 15,526. In side-by-side comparisons, plants of the new *Lobelia* differ primarily from plants of 'Loboudtis' in the following characteristics:

1. Plants of the new *Lobelia* are more freely flowering than plants of 'Loboudtis'.
2. Plants of the new *Lobelia* have larger flowers than plants of 'Loboudtis'.
3. Plants of the new *Lobelia* flower more freely and for a longer period of time under high temperature conditions than plants of 'Loboudtis'.

Plants of the new *Lobelia* can also be compared to plants of *Lobelia erinus* 'Tech Helitbule', disclosed in U.S. Plant Pat. No. 19,067. In side-by-side comparisons, plants of the new *Lobelia* differ primarily from plants of 'Tech Helitbule' in the following characteristics:

1. Plants of the new *Lobelia* are more trailing than plants of 'Tech Helitbule'.
2. Plants of the new *Lobelia* have larger flowers than plants of 'Tech Helitbule'.
3. Flowers of plants of the new *Lobelia* are pure white in color whereas flowers of plants of 'Tech Helitbule' are light blue in color.
4. Plants of the new *Lobelia* flower more freely under high temperature conditions than plants of 'Tech Helitbule'.

BRIEF DESCRIPTION OF THE PHOTOGRAPHS

The accompanying colored photographs illustrate the overall appearance of the new *Lobelia* plant showing the colors as true as it is reasonably possible to obtain in colored reproductions of this type. Colors in the photographs may differ slightly from the color values cited in the detailed botanical description which accurately describe the actual colors of the new *Lobelia* plant.

The photograph on the first sheet (FIG. 1) is a side perspective view of a typical flowering plant of 'WNLOLACLWH' grown in a container.

Figure 2:
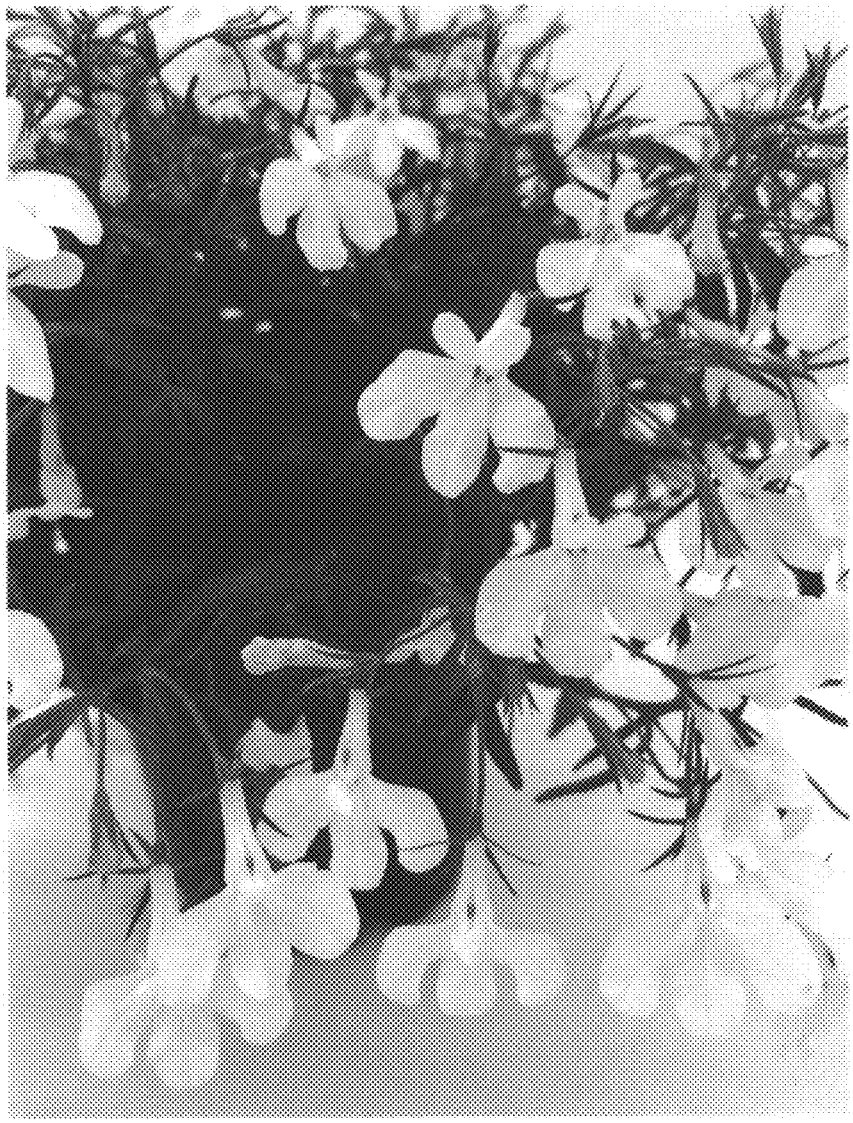

The photograph on the second sheet (FIG. 2) is a close-up view of a typical flowering plant of 'WNLOLACLWH'.

DETAILED BOTANICAL DESCRIPTION

The aforementioned photographs and following observations and measurements describe plants grown during the autumn and winter in 10.8-cm containers in a glass-covered greenhouse in Loudon, N.H. and under cultural practices typical of commercial *Lobelia* production. During the production of the plants, day and night temperatures averaged 18° C. Plants were grown under long day/short night conditions and were pinched two weeks after planting. Plants were ten weeks from planting rooted cuttings when the photographs and description were taken. In the following description, color references are made to The Royal Horticultural Society Colour Chart, 2015 Edition, except where general terms of ordinary dictionary significance are used.

Botanical classification: *Lobelia erinus* 'WNLOLACLWH'.

Parentage:

*Female, or seed, parent.*—*Lobelia erinus* 'Tech Hewhit', disclosed in U.S. Plant Pat. No. 19,053.

*Male, or pollen, parent.*—*Lobelia erinus* 'Weslosnowhi', not patented.

Propagation:

*Type cutting.*—Vegetative terminal cuttings.

*Time to initiate roots, summer.*—About seven days at soil temperatures about 21° C. to 24° C.

*Time to initiate roots, winter.*—About ten days at soil temperatures about 18° C. to 21° C.

*Time to produce a rooted young plant, summer.*—About four weeks at soil temperatures about 21° C. to 24° C.

*Time to produce a rooted young plant, winter.*—About five weeks at soil temperatures about 16° C. to 18° C.

*Root description.*—Fine, fibrous; typically white in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Upright to outwardly spreading and mounding to trailing plant habit; freely branching habit with lateral branches developing at potentially every node; dense and bushy plant habit; vigorous and sturdy growth habit and rapid growth rate.

*Plant height.*—About 14 cm.

*Plant width.*—About 37 cm.

*Lateral branch description.*—Length: About 21 cm. Diameter: About 3 mm. Internode length: About 1 cm. Strength: Strong, flexible. Aspect: Upright to outwardly spreading to trailing. Texture and luster: Fine pubescence, dense; moderately glossy. Color: Close to 146A.

Leaf description:

*Arrangement.*—Alternate, simple.

*Length.*—About 2.75 cm.

*Width.*—About 1.75 cm.

*Shape.*—Lanceolate becoming more elliptic with development.

*Apex.*—Obtuse to bluntly acute.

*Base.*—Cuneate.

*Margin.*—Crenate; slightly undulate.

*Texture and luster, upper and lower surfaces.*—Smooth, glabrous; moderately glossy.

*Venation pattern.*—Pinnate.

*Color.*—Developing leaves, upper surface: Close to 147A. Developing leaves, lower surface: Close to 146A. Fully expanded leaves, upper surface: Close to 147A; venation, close to between 146A and 147A. Fully expanded leaves, lower surface: Close to 147B; venation, close to 146A.

*Petioles.*—Length: About 7.5 mm. Diameter: About 2 mm. Texture and luster: Smooth, glabrous; moderately glossy. Color, upper and lower surfaces: Close to 146A.

Flower description:

*Flower arrangement, habit and shape.*—Single, axillary flowers; flowers face upright to outwardly; freely flowering habit with flowers potentially developing at every node; flowers bilabiate with two upper petals and three larger fused lower petals.

*Fragrance.*—Faint; pleasant.

*Natural flowering season.*—Long flowering period, in New Hampshire, plants of the new *Lobelia* flower continuously from planting in the spring until frost in the autumn; early flowering habit, plants begin flowering about three to four weeks after planting.

*Flower longevity on the plant*.—Longevity of individual flowers is highly dependent on temperature, flowers typically last about 10 to 14 days on the plant; flowers persistent.

*Flower height*.—About 2 cm to 2.4 cm.

*Flower diameter*.—About 2.1 cm by 2.3 cm.

*Flower depth*.—About 2 cm to 2.5 cm.

*Flower throat diameter*.—About 2 mm to 3 mm.

*Flower tube length*.—About 1 cm to 1.2 cm.

*Flower tube diameter, distally*.—About 3.5 mm to 4 mm.

*Flower tube diameter, proximally*.—About 2 mm to 2.5 mm.

*Flower buds*.—Length: About 9 mm. Diameter: About 2.5 mm. Shape: Obovate. Color: Sepals, more green than 147A; petals, close to 144B to 144C.

*Petals*.—Arrangement: Single whorl of five petals fused towards the base; two upper petals and three larger fused lower petals. Upper petals: Length, beyond throat: About 7.5 mm. Width: About 3 mm. Shape: Oblanceolate. Apex: Cuspidate. Margin: Entire; not undulate. Texture and luster, upper and lower surfaces: Smooth, glabrous; matte. Lower petals: Length, beyond throat: About 1.4 cm. Width: About 8 mm. Shape: Obovate. Apex: Obtuse to short cuspidate. Margin: Entire; not undulate. Texture and luster, upper and lower surfaces: Smooth, glabrous; matte. Color, upper and lower petals: When opening and fully opened, upper surface: Close to NN155D; venation, close to NN155D; color does not change with subsequent development. When opening and fully opened, lower surface: Close to NN155D; venation, close to NN155D; color does not change with subsequent development. Color, throat, upper petals: Close to NN155D. Color, throat, lower petals: Close to NN155D; nectar guides, close to 144A. Color, tube, upper and lower petals: Close to NN155D.

*Sepals*.—Arrangement: Single whorl of five sepals, fused at the base; star-shaped calyx. Length: About 7.5 mm. Width: About 1 mm. Shape: Acicular. Apex: Acute. Margin: Entire; not undulate. Texture and luster, upper and lower surfaces: Smooth, glabrous; slightly glossy. Color, upper and lower surfaces: More green than 147A.

*Peduncles*.—Length: About 2.2 cm. Diameter: Less than 1 mm. Strength: Strong, flexible; wiry. Aspect: About 45° to 90° from lateral branch axis. Texture and luster: Smooth, glabrous; slightly glossy. Color: Slightly darker green than 146A.

*Reproductive organs*.—Stamens: Quantity per flower: Five. Filament length: About 8 mm. Filament color: Close to NN155D. Anther size: About 0.5 mm by 2 mm. Anther shape: Oblong. Anther color: Close to 164A. Pollen amount: None observed. Pistils: Quantity per flower: One. Pistil length: About 1 cm. Stigma shape: Globose. Stigma color: Close to 84A. Style color: Close to 144A. Ovary color: Close to 144A.

*Fruits and seeds*.—To date, fruit and seed development have not been observed on plants of the new *Lobelia*.

Pathogen & pest resistance: To date, plants of the new *Lobelia* have not been noted to be resistant to pathogens and pests common to *Lobelia* plants.

Garden performance: Plants of the new *Lobelia* have been observed to have good garden performance and to tolerate wind, rain and to be relatively tolerant to high temperature conditions.

It is claimed:

1. A new and distinct *Lobelia* plant named 'WNLOLA-CLWH' as illustrated and described.

* * * * *